United States Patent [19]

Covey et al.

[11] Patent Number: 4,547,068

[45] Date of Patent: Oct. 15, 1985

[54] OPTICAL ANALYTICAL INSTRUMENT BEAM CONDENSER

[76] Inventors: Joel P. Covey, 2110 Westbrook La.; D. Warren Vidrine, 4901 Chalet Gardens Rd. #209, both of Madison, Wis. 53711

[21] Appl. No.: 472,026

[22] Filed: Mar. 4, 1983

[51] Int. Cl.[4] ............................................. G01N 21/01
[52] U.S. Cl. ..................................... 356/244; 356/346
[58] Field of Search ............................... 356/346, 244

[56] References Cited

U.S. PATENT DOCUMENTS 3,868,185  2/1975  Genzel et al. ..................... 356/346
3,972,618  8/1976  Hawes ............................. 356/345

Primary Examiner—Davis L. Willis
Assistant Examiner—Matthew W. Koren
Attorney, Agent, or Firm—Kinney & Lange

[57] ABSTRACT

An analytical instrument including a source of analytical radiation, a support for a sample to be analyzed, an analytical radiation detector and optical elements for directing the analytical radiation within the instrument including a beam condenser system having elements for focusing the radiation relative to the sample support and the detector and elements for collimating radiation focused relative to the sample support and deflecting it for focusing on the detector. The collimating and deflecting elements are supported for common movement in a first direction with the collimating element being supported for movement, independently of the deflecting element, in a second direction orthogonal to the first direction. The collimating and deflecting elements may each be reflecting elements or the collimating element may be a refracting element. The sample support may be movable in two directions coordinated with the directions of movement of the collimating and deflecting elements and may be adapted to accept an ATR crystal. The sample support and beam condenser system may be contained in a dedicated sample compartment with the movement(s) of the collimating and deflecting elements compensating for differences in the thickness of samples supported by the sample support and for differences in optical path to and from a sample supported by the sample support.

11 Claims, 3 Drawing Figures

OPTICAL ANALYTICAL INSTRUMENT BEAM CONDENSER

DESCRIPTION

BACKGROUND OF THE INVENTION

Optical analytical instruments are known to the prior art. Typically such instruments include a source of analytical radiation, a detector for the radiation, a system for supporting a sample to be analyzed and optical elements for directing the radiation along an optical path of the instrument. The present invention relates to an improved beam condenser system for such an instrument.

In the prior art, beam condensers are often employed to improve the sensitivity of the instrument. For example, the available sources of some desired analytical radiation have practical limits as to their power. An example of such an analytical radiation limitation within an analytical instrument is found in the context of an infrared spectrometer employing an interferometer within its operating system. Since there is a practical limit to the intensity of infrared sources, it has become the practice to condense the analytical beam at the sample, thereby concentrating it and improving the signal to noise ratio. However, in the prior art, this has required tedious and time-consuming alignment and realignment of the condenser optical elements as a result of the many interactive alignments that are necessary. Even a highly skilled and experienced operator has difficulty duplicating the theoretical "throughput" when such systems are employed.

In addition to concentrations of the analytical radiation, other applications wherein beam condenser systems have advantage are in the analysis of small samples, the use of attenuated total reflectance (ATR) crystals for the study of surface effects and in the mapping or profiling of a sample, particularly an inhomogeneous sample. Beam condenser systems employed in the prior art for these purposes have the deficiencies noted above.

BRIEF SUMMARY OF THE INVENTION

The present invention provides an improved beam condenser system for use in an analytical instrument of the type having a source of analytical radiation, an analytical radiation detector and a sample support. The improved beam condenser system of the present invention includes optical elements for directing the analytical radiation along an optical path to the sample support, including a first optical element for focusing the radiation relative to the sample support, and from the sample support to the radiation detector, including an optical element for focusing the analytical radiation relative to the radiation detector. This last mentioned focusing element is of a type commonly employed with detectors known to the prior art and has as its purpose an enhancement of detector response, including an elimination or reduction of edge effects. For the purpose of this specification and claims, the concept of focusing relative to the detector requires nothing more than properly shaping and directing the analytical radiation to the detector in a manner known to the prior art.

The optical elements forming the improved condenser system of the present invention, in addition to those noted above, includes an element for collimating analytical radiation that has been focused relative to the sample support and a second element for deflecting the radiation collimating by the collimating element to the detector focusing element. The collimating and deflecting elements are supported for common movement in a first direction with the collimating element being supported for movement, independently of the deflecting element, in a second direction orthogonal to the first direction. In a preferred embodiment the sample support is movable in two directions, the sample support movement directions be coordinated with the direction of movement of the collimating and deflecting elements. The deflecting element may be a reflecting element while the collimating element may be either a refracting or reflecting element. Movement of the collimating element may be employed to compensate for differences in the thicknesses of samples supported by the sample support as well as to compensate for differences in optical paths to and from a sample supported by the sample support. The movement of the deflecting element is employed to align collimating radiation from the collimating element with the focusing element with the detector.

DETAILED DESCRIPTION OF DRAWINGS

The optical elements of choice within an analytical instrument in accordance with the present invention depend largely on the efficiency of the elements relative to the wave length or frequencies in question. For example, mirrors or reflecting elements are often the elements of choice, relative to lenses or refracting elements, because of their greater efficiency with a particular radiation. Efficiency is of particular interest in the context of infrared spectroscopy in that practical infrared sources are of relatively low energy. Since greater intensity at the sample improves instrument sensitivity, an implementation of the present invention with the most efficient optical elements is preferred. For this reason, and within the context of an infrared spectrometer, the preferred embodiment illustrated in FIG. 1 employs reflecting elements.

Figure 1:
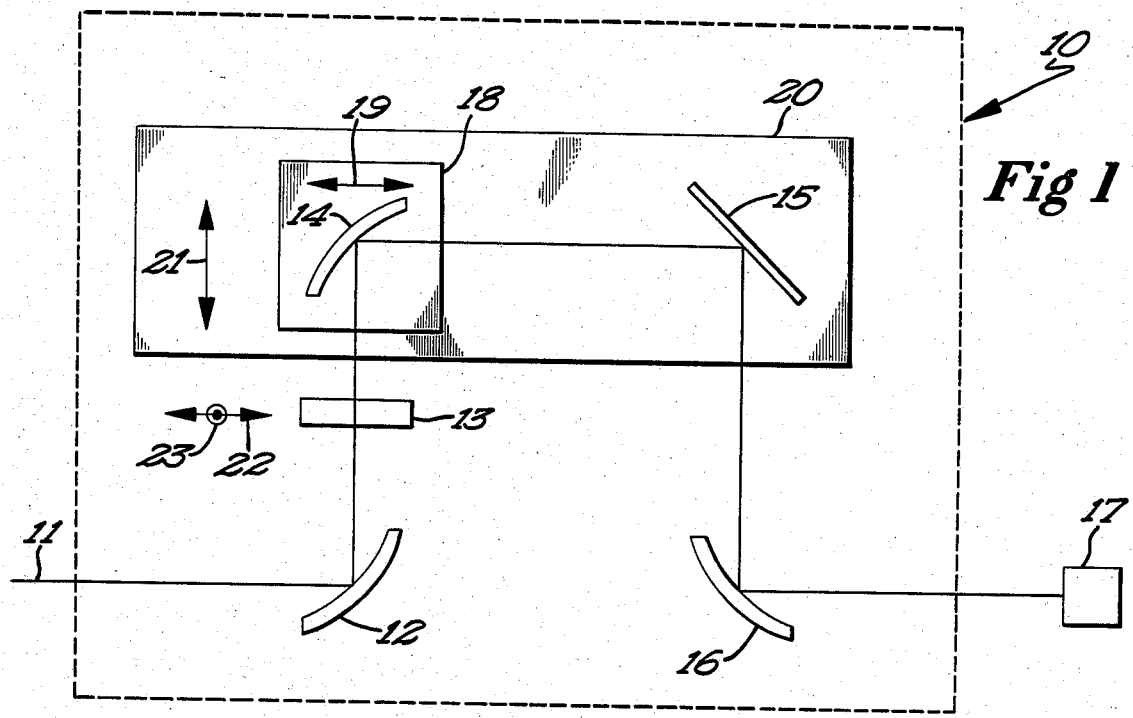
FIG. 1 is a diagramatic illustration of a preferred embodiment of the present invention.

The phantom box 10 in FIG. 1 designates a dedicated sample compartment which may be purged in the manner known to the prior art as with dry air or nitrogen, for example. As is known, this has the purpose of factoring out the effects of moisture and carbon dioxide. In some instances, however, the present invention may be implemented without a dedicated sample compartment.

A collimated beam of analytical radiation 11 enters the sample compartment 10 and impinges on a reflecting element 12 from which it is directed to a sample holder 13. Reflecting element 12 is a focusing element and, preferably, is a parabolic reflector having a particular focal point relative to the sample holder 13. Focal point determination is known. The optical path illustrated in FIG. 1 extends from the sample holder 13 to a collimating reflecting element 14 and from the collimating element 14 to a deflecting element 15. The collimating element 14 is preferably a parabolic reflector while the reflecting element 15 is a planar reflecting surface. The collimated light from the deflecting element 15 is directed to a focusing reflecting element 16 by which it is focused on a detector 17. Detector 17 may be any convenient detector known to the prior art.

The reflecting element 14 is supported for movement with a platform 18, movement being in the directions of the arrows 19. The platform 18 and the deflecting element 15 are supported for common movement on a platform 20, the directions of movement of the platform 20 being indicated by the arrows 21. For reasons to be described below, the sample support 13 is movable in directions which coordinate with the movement of the elements 14 and 15. This movement includes movement in a first direction generally parallel to the directions 19 of platform 18, as indicated at 22, and in directions perpendicular to the plane of the drawing sheet as indicated at 23 in FIG. 1.

Platforms 18 and 20 may be supported for movement and moved in any convenient manner, the platform 18 being moved commonly with the element 15 on movement of the platform 20 in the direction of the arrows 21. Movement of the platform 18 in the directions of the arrows 19 is independent of the movement of the platform 20 and the element 15 it supports. In this manner, the platform 20 may be moved to adjust for differences in the optical thickness of samples supported by the sample support 13 while maintaining the optical relationship between the collimating element 14, and its collimated outlet beam, and the focusing element 16 through movement of the deflecting element 15 with the element 14. However, movement of the platform 18 in the directions of the arrows 19 may be employed to provide an offset in the beam position to compensate for differences in optical path to and from a sample supported by the sample support 13. This optical path compensation has particular application in the instance of ATR crystal analysis.

Figure 2:
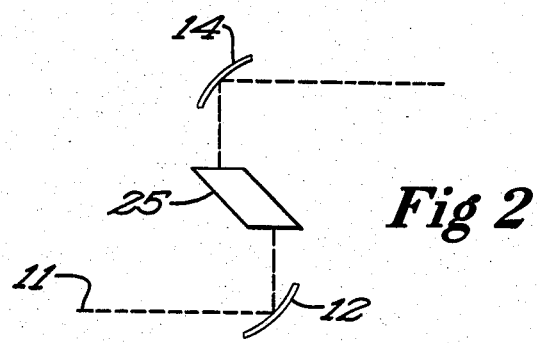
FIG. 2 illustrates a particular application of the embodiment of FIG. 1.

A set-up of a portion of the embodiment of FIG. 1 is illustrated in FIG. 2 for the purpose of ATR analysis. In FIG. 2, an ATR crystal 25 is supported by the sample support 13 (not shown in FIG. 2) with the sample support 13 being positioned such that a collimated beam of light 11 is properly focused by the element 12 relative to the entry face of the crystal 12. In FIG. 2, the platform 18 has been moved to properly position the element 14 relative to the exit face of the crystal 25, which proper position may also require a movement of the platform 20 and, thus, movement of the reflecting element 15. As illustrated in FIG. 2, the coordinated movement between the sample support 13, platform 18 and platform 20 facilitates the set up of the relative position of the elements within the sample compartment 10. The constraints on those movements provided by the attending supporting structures reduces the tedious alignments and realignments of prior art set ups of beam condenser systems. The supporting structure and motion imparting systems for the sample support 13, platform 18 and platform 20 may be any known to the prior art it being presently contemplated that stepper motors will be employed as the motion imparting mechanisms to facilitate precise control of the relative position of the illustrated optical elements to each other.

Figure 3:
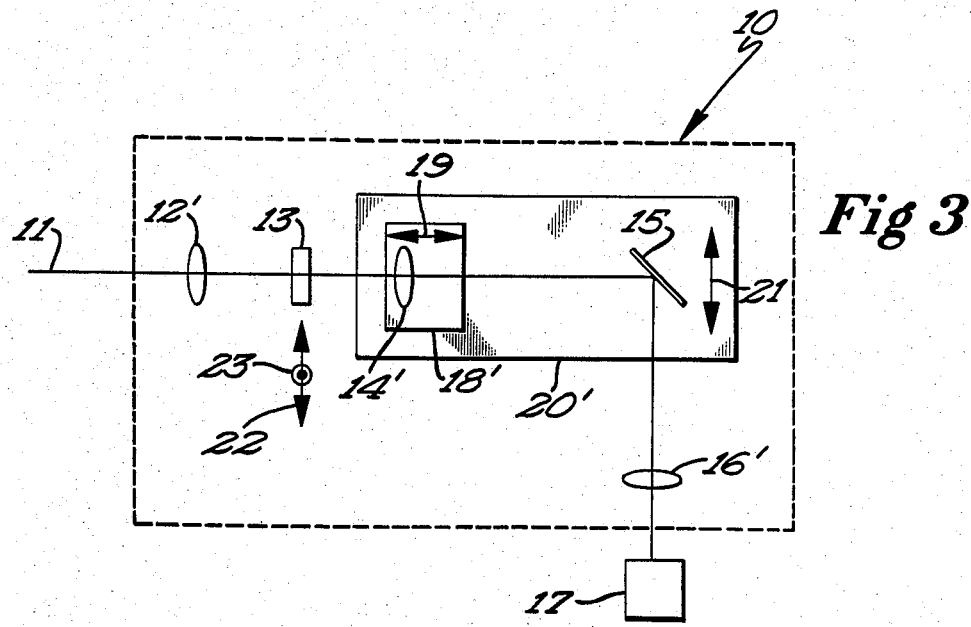
FIG. 3 is an alternative preferred embodiment to the embodiment illustrated in FIG. 1.

Obviously many modifications and variations of the present invention are possible in light of the above teachings. For example, the motions of the platforms 18 and 20 may be restricted to those illustrated by arrows 19 and 21 to restrict the need to alignment after initial set-up. However, any motion imparting system may be employed so long as the actual relative position of each platform, and their associated optical element can be readily determined and automatically controlled. Indeed, it is automatic control that is a major accomplishment provided by the present invention. FIG. 3 illustrates a refracting element implementation of the present invention with functionally similar elements being indicated by primed reference numerals corresponding to the reference numerals of similar elements in the other figures. It is, therefore, to be understood that, within the scope of the appended claims, the invention may be practiced otherwise than as specifically described.

What is claimed is:

1. In an analytical instrument of the type having a source of analytical radiation, having means for detecting said analytical radiation and having means for supporting a sample to be analyzed, an improved beam condenser system having optical elements directing said analytical radiation along an optical path to said sample supporting means, including first means for focusing said analytical radiation relative to said sample supporting means, and from said sample supporting means to said radiation detecting means, including second means for focusing said analytical radiation relative to said radiation detecting means, said optical elements further comprising means for collimating analytical radiation focused by said first means and means for deflecting analytical radiation collimated by said collimating means to said second means, said collimating means and deflecting means being supported for common movement in a first direction and said collimating means being supported for movement, independently of said deflecting means, in a second direction orthogonal to said first direction.

2. The analytical instrument of claim 1 wherein said collimating and deflecting means each comprise reflecting elements.

3. The analytical instrument of claim 2 wherein said sample supporting means is movable in said second direction.

4. The analytical instrument of claim 2 wherein said sample supporting means is movable in said second direction and movable in a third direction orthogonal to said first and second directions.

5. The analytical instrument of claim 1 wherein said collimating means comprises refracting means and said deflecting means comprises reflecting means.

6. The analytical instrument of claim 5 wherein said supporting means is movable in said first direction.

7. The analytical instrument of claim 5 wherein said sample supporting means is movable in said first direction and movable in a third direction orthogonal to said first and second directions.

8. The analytical instrument of claim 1 wherein said collimating means is carried for movement in said second direction by first support means, said first support means and said deflecting means being carried for movement in said first direction by second support means.

9. The analytical instrument of claim 1 wherein said sample supporting means comprises means for supporting an ATR crystal.

10. The analytical instrument of claim 1 wherein said sample supporting means and beam condenser system are contained in a dedicated sample compartment forming a part of said instrument.

11. The analytical instrument of claim 1 wherein movement of said collimating means in one of said first and second directions compensates for differences in the thickness of samples supported by said sample supporting means and movement in the other of said directions compensates for differences in optical path to and from samples supported by said sample supporting means.

* * * * *